United States Patent [19]

Losada et al.

[11] Patent Number: 4,690,153

[45] Date of Patent: Sep. 1, 1987

[54] FLOW INDUCING MEANS FOR SMALL VOLUME CONTAINERS

[75] Inventors: Robert J. Losada, Astoria, N.Y.; Hugh T. Conway, Verona, N.J.

[73] Assignee: Becton, Dickinson and Company, Franklin Lakes, N.J.

[21] Appl. No.: 803,050

[22] Filed: Nov. 29, 1985

[51] Int. Cl.$^4$ .............................................. A61B 5/14
[52] U.S. Cl. .................................... 128/763; 128/770
[58] Field of Search ............................... 128/763–770; 604/317, 411, 414; 73/864.01, 864.02

[56] References Cited

U.S. PATENT DOCUMENTS

| | | | |
|---|---|---|---|
| 3,952,599 | 4/1976 | Ayres | 73/864.02 |
| 4,024,857 | 5/1977 | Blecher et al. | 128/763 |
| 4,050,451 | 9/1977 | Columbus | 128/764 |
| 4,215,700 | 8/1980 | Crouther et al. | 128/763 |
| 4,397,318 | 8/1983 | Burns | 128/763 |
| 4,411,163 | 10/1983 | White | 128/767 |

FOREIGN PATENT DOCUMENTS 1288383 12/1962 France ........................ 128/766

*Primary Examiner*—Kyle L. Howell
*Assistant Examiner*—Max F. Hindenburg
*Attorney, Agent, or Firm*—Robert P. Grindle

[57] ABSTRACT

An arrangement is provided for inducing rapid flow of a blood sample into a collection assembly for the sample, with the arrangement including an elongated member of narrow width positioned in the flow path of the blood from the source therefore to the collection area therefore. The member of the invention may be, for example, an elongated flat strip, flexible or rigid, a solid rod, a solid strip square in cross section, or a tubular rod. The elongated device may be separate and positioned or adhered to a surface forming the blood flow path or it may be molded simultaneously with a collection assembly. The device may serve to provide a bridging transition from the surface of one part of an assembly to another. Finally, the device may be used to induce sample flow back and forth in a collection tube during mixing.

7 Claims, 5 Drawing Figures

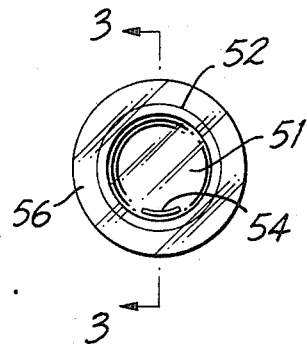
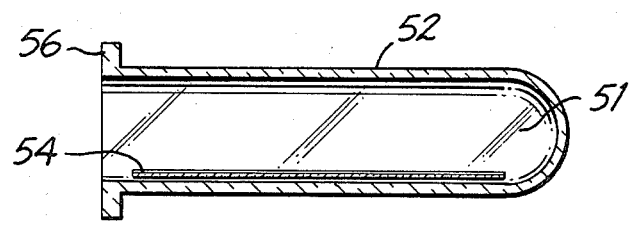
FIG. 3(a)    FIG. 3(b)
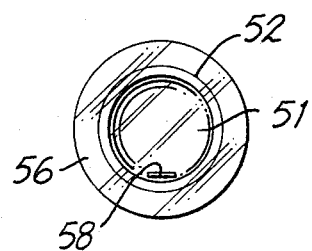
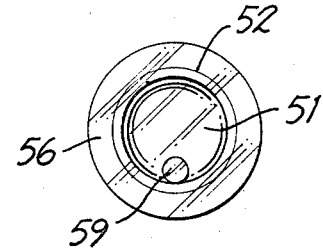
FIG. 4(a)    FIG. 4(b)
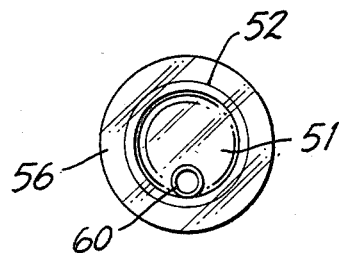
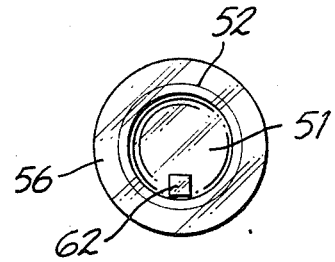
FIG. 4(c)    FIG. 4(d)

FLOW INDUCING MEANS FOR SMALL VOLUME CONTAINERS

BACKGROUND AND STATEMENT OF THE INVENTION

This invention relates to a blood collection assembly incorporating a microcollection container. The invention is an improvement over the collection assembly described and claimed in U.S. Pat. No. 4,397,318, issued Aug. 9, 1983, which is hereby incorporated by reference in its entirety. This invention is related, also, to the inventions described and claimed in co-pending U.S. patent applications Ser. No. 743,250 and 743,534, both filed June 11, 1985. Referance should be made to the patent and the applications for background information concerning the teachings of the invention here. The earlier patent involved the use of a scoop collector for connection to a blood microcollection container for engaging a puncture would to obtain a blood sample from an individual for subsequent examination of that sample for the determination of the presence or absence of some disease or other problem in a patient. The scoop-type blood collection device provides a substantially larger engaging surface for engaging the puncture for collecting the blood, and a substantially larger transfer surface for rapidly transferring the blood from the collector into the microcollection container. Because of the relatively large engaging surface for engaging the puncture wound, the arrangement does not require a precise positioning of the scoop engaging surface in order to initiate and rapidly transfer a quantity of blood to the microcollection container.

As will be appreciated by practitioners-in-the-art, recent advancements in analytical instrumentation have made it possible to carry out a variety of hematological or chemical diagnostic procedures on very small quantities of blood. Because of this, a patient's finger, earlobe, or infant's heel may be punctured and a very small quantity of blood rapidly collected into a microcollection container for such testing. Such arrangements obviate the need to withdraw venous blood from patients. However, such collection arrangements must be such that the blood is rapidly collected prior to any coagulation thereof.

In the past, prior to the scoop collector disclosed in the above-noted U.S. Pat. No. 4,397,318, a cap or top arrangement was configured to fit on the top of a microcollection container with the top having an integral capillary tube for engaging the puncture and transferring blood to the container. However, with such an arrangement, the tip of the capillary tube had to be arranged precisely adjacent the puncture wound and the entire apparatus had to be so positioned that the blood flow along the bottom surface of the tubular microcollection container moved continuously in order to engage the surface of the container. Otherwise, if a precise positioning was not carried out, capillary action was not initiated or slowed with subsequent clotting. Such collectors are described in U.S. Pat. No. 4,024,857, issued May 24, 1977.

One problem with the scoop collector taught and claimed in U.S. Pat. No. 4,397,318, although the arrangement taught therein is highly efficient for the rapid collection of a blood sample into a microcollection container, is the fact that because of the very rapid collection of blood by the scoop collector, the separate blood passage in the collector becomes somewhat occluded by the blood passing therethrough and there is "hang-up" on the walls thereof by capillary action. While this phenomenon is only momentary, it can delay blood collection in situations where the technician is, for example, attempting to take a blood sample from a screaming, wiggly baby.

With this invention, by contrast, a separate or integral elongated blood flow inducing member is provided which serves as a guide for inducing blood flow passage along a surface, and as a bridge, inducing blood flow across a transition point between two parts in a blood collection assembly. Representative blood flow inducing members include, for example, an elongated rod or strip arrangement incorporated into a blood microcollection assembly in such a way that the collected blood is guided from the collector continuously into the associated collection container. For this reason, capillary action causing blood "hang-up" does not take place and blood flows rapidly through the collector into the collection tube or reservoir passage. This in turn reduces blood sample waste in the very small total quantities involved, resulting in a larger specimen yield. As a further feature of the invention here, in the blood collection tube, once a sample is collected there and the tube closed, the invention induces flow of the sample back and forth to enhance mixing of the collected sample with other components in the tube. Moreover, such an arrangement reduces the need for incorporating expensive wetting agents in the collector devices of the invention, either as a component of the material forming the devices or as a separately applied surfactant. Also, there is an avoidance of any reaction between the wetting agents and the sample being collected.

In order to enhance the movement of blood through the collector arrangements as taught in the above-noted patent and co-pending applications, this invention includes separate members such as rods or strips. Alternatively, elongated flow inducing members may be formed during the molding of the blood collection assembly parts. They are positioned in the collector and along the walls of the tube in which the specimen is taken. Thus, the invention induces sequentially, rapid flow in the collector, provides rapid bridging or transition of that flow from the collector to the tube wall, and finally, rapid flow along the tube wall to the bottom thereof.

As purely illustrative of materials and dimensions of the flow inducing member of the invention, a single film strip of flexible material comprised of polyethylene film may be 0.05 millimeters (mm) thick and 1.52 mm wide. A rigid polypropylene strip may be 0.25 mm thick and 0.91 mm wide. A solid rod may be comprised of polytetrafluoroethylene and have a diameter of 0.76 mm. A tube-shaped strip may be comprised of glass with an O.D. of 0.91 mm. The length will vary depending upon the different applications to be described below.

The elongated flow inducing members of the invention in the form of integral or separate rods, strips or indentations provide a continuous flow inducing or guiding surface for the sample being collected from the initial puncture wound to the final reservoir and they may be separately formed, and either merely positioned or adhered to the walls of the objects involved, or they may be incorporated into the molds forming the objects themselves. As mentioned above, the invention may be in the form of flat strips, or they may be square, round, or semi-round objects in cross-section. In addition, they may take the form of indentations in the walls, for example, of a collection tube, or the collector.

Other objects and advantages of this invention will be apparent from the following description, the accompanying drawings and the appended claims.

DESCRIPTION OF THE DRAWINGS

FIG. 3(a) is a cross-sectional view of the blood collection reservoir of the invention illustrating an additional embodiment thereof;

FIG. 3(b) is a longitudinal sectional view of the blood collection reservoir of 3(a) taken along lines 3—3 thereof;

FIGS. 4(a), 4(b), 4(c), and 4(d) are end views of the open end of a blood collection reservoir showing different embodiments of the invention in section.

DETAILED DESCRIPTION OF THE INVENTION

Figure 1:
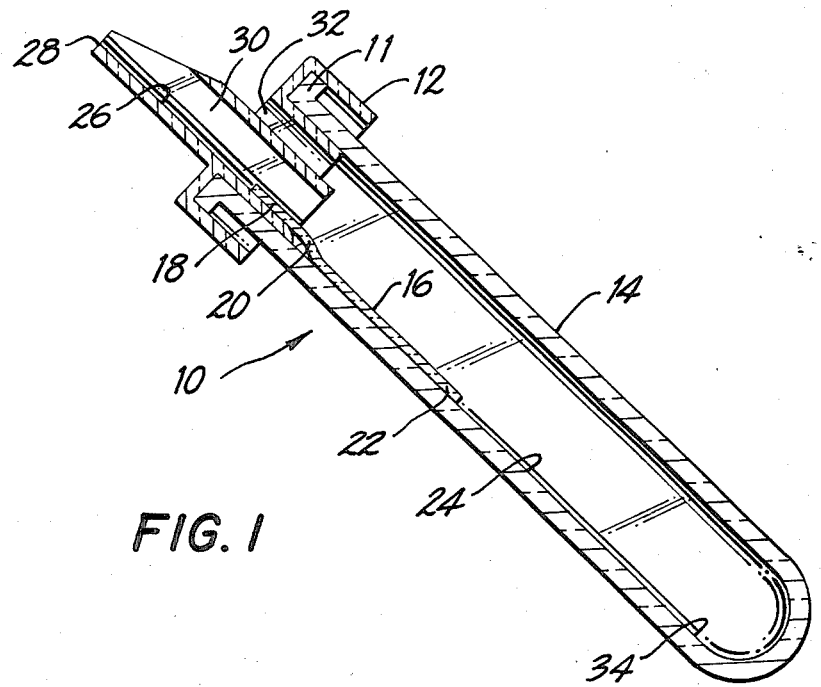
FIG. 1 is a longitudinal sectional view of a blood collection assembly incorporating one embodiment of the invention in the form of a flat filmlike strip acting as a transitional member between the collector for the assembly and the reservoir for the assembly in order to guide a collected volume of blood from one to the other.

Referring to the drawings in which like characters of reference refer to like parts throughout the several views thereof, FIG. 1 illustrates the invention as employed in a blood collection assembly utilizing a scoop collector as taught and claimed in the above noted U.S. Pat. No. 4,397,318 which scoop collector is attached to the open end 11 of a blood collection reservoir or tube 14, with the collector 12 and the reservoir 14 combining to form a blood collection assembly 10. It should be understood that this is the form of a microcollection assembly as practitioners-in-the-art will understand.

The assembly, as shown in FIG. 1, incorporates the invention in the form of a film strip 18 one end of which is partially adhered to surface 26 of collector 12 and extends along the surface 24 of reservoir 14. While strip 18 is adhered to surface 26, it is to be understood that it is within the purview of this invention that the elongated flow inducing member may be merely positioned without adherence in desired locations in a collection assembly. The strip 18 serves to provide a transition or bridge across the inner end of the inner surface 26 of collector 12 onto the surface 24 of reservoir 14 at the transition point 20 thereof. Thus, when blood is collected at the scoop end 28 of collector 12, it flows rapidly through the area 30 in collector 12 and comes in contact with the strip 18 which serves to induce and lead the blood sample rapidly across transition point 20 and into and across the surface 24 to the bottom 34 of reservoir 14. When this is happening, of course, as is taught in the above noted U.S. patent, air which is displaced when the blood sample is introduced into the reservoir 14 escapes through vent 32 in collector 12.

Figures 2A, 2B:
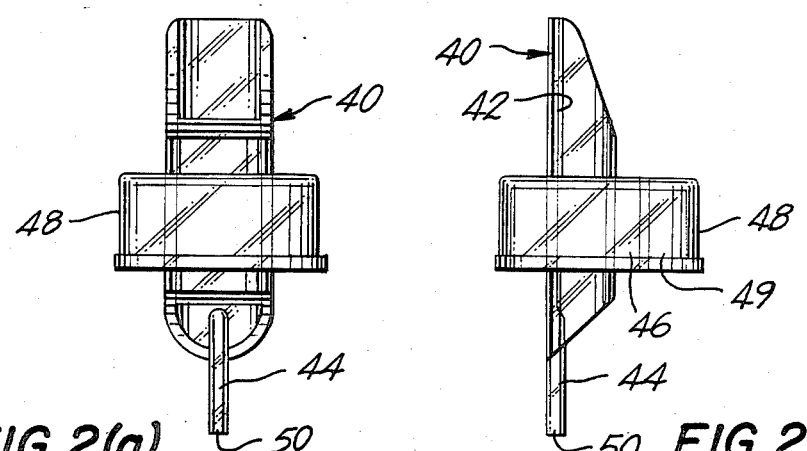
FIGS. 2(a); 2(b) and 2(c) are a top plan view, a side view and end view of a collector for a blood collection assembly incorporating a molded rod as an additional embodiment of the invention.
Figure 2C:
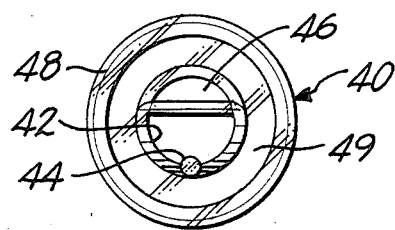

Referring not to the embodiment shown in FIGS. 2(a), 2(b) and 2(c), a collector 40 is shown similar to the collector 12 described in FIG. 1, However, collector 40 has incorporated therein one form of the elongated blood flow inducing member of the invention as a molded in place rod 44. That is, when the mold is prepared for formulating a plurality of collectors 40 for mass production, the mold includes provision for the molded rod 44. Collector 40 includes the vent area 46 in the same manner as the vent in collector 12 noted above with the annular skirt 448 which serves to provide a space 49 for the friction fit of the open end of a collector reservoir 14. Thus, the molded-in rod in the embodiment shown in the FIGS. 2(a), 2(b) and 2(c) serves to provide the transitional guiding surface for inducing flow of a blood sample passing along the surface 42 of collector 40 with the end 50 being positioned adjacent the internal surface of the associated reservoir when the collector is fitted in place on the open end of the reservoir in the same manner as described in FIG. 1 above.

Referring now to FIG. 3, a longitudinal sectional view of a blood collection reservoir 52 is shown. It will be understood by practitioners-in-the-art that the reservoir 52 is a microcollection container for receiving minute quantities of blood drawn from a puncture wound in the finger, ear or in the case of infants, perhaps, in the heel. It is important that the blood be collected rapidly from this wound and introduced into the tube or reservoir 52 toward the bottom 51 thereof for subsequent testing of the blood sample. It is important that the blood be drawn and introduced into these very small tubes as rapidly as possible prior to the coagulation thereof. Thus, as shown in FIG. 3, a flexible filmstrip 54 is shown positioned along the internal surface of tube 52. In this case, a collector, as described above, would be fitted on the rim 56 of the open end of the tube 52 so as to introduce into reservoir 52 a blood sample. In this case, the strip is positioned along the tube's internal surface in order to induce and guide the flow of the blood sample to the closed end thereof as rapidly as possible. Because of the strip 54 of the invention, the blood sample does not "hang-up" along the internal surface of tube 52 and slow up the collection of the blood sample. Moreover, once tube 52 is stoppered, strip 54 induces flow of the sample back and forth to enhance a desired mixing action. FIG. 3(a) shows the end view of the reservoir or tube 52 shown in FIG. 3. This view shows the configuration and lateral extent of flexible film strip 54 as positioned in tube 52.

Referring now to FIGS. 4(a), 4(b), 4(c), and 4(d), these figures show additional embodiments and configurations of separate elongated blood flow inducing members of the invention. Thus, FIG. 4(a) shows a rigid film strip 58, as opposed to the flexible film strip described in FIGS. 3 and 3(a) above. Film strip 58, as is shown in FIG. 4(a), retains original shape across lateral cross-section, as opposed to the conforming configuration shown of film strip 54 in FIGS. 3 and 3(a). FIG. 4(b) shows the embodiment of the invention in the form of a round rod 59 while FIG. 4(c) shows a round rod in the form of a hollow tubular rod 60, as opposed to a solid rod 59. FIG. 4(d) shows a rectangular solid rod 62.

While these various embodiments shown in the description above may be adhered to the internal surface of a blood collection reservoir such as 52 shown in FIG. 3, preferably they will be merely positioned as required as separate components without any physical adherence. It will be understood, further, by practitioners-in-the-art of the manufacture of such collection tubes that these various embodiments may be incorporated into a mold during the formation of such tubes, as discussed above.

Figures 5A, 5B:
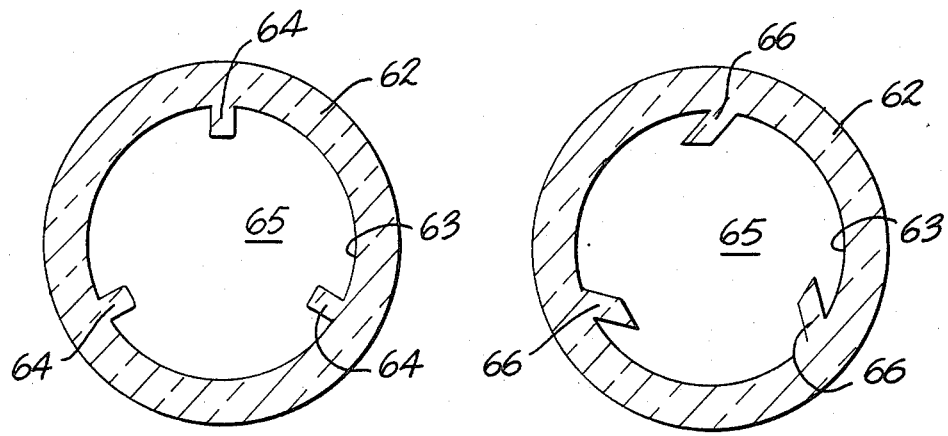
FIGS. 5(a), 5(b), 5(c), 5(d) and 5(e) are end views of the open end of the blood collection reservoir showing additional embodiments of the invention in section.

Thus, as shown in FIGS. 5(a), 5(b), 5(c), 5(d) and 5(e), various forms of the elongated blood flow inducing members of the invention are shown in a blood collection reservoir 65 with an end rim 62, with the collector having incorporated therein during the formation thereof, an elongated molded in arrangement for inducing and directing the flow of blood along the internal surface 63 thereof. Thus, as shown in FIG. 5(a), three rectangular protrusions 64 are shown spaced equally around the circumference of a surface 63. These protrusions extend along the longitudinal extend of the reservoir 65 in the same manner as shown in FIG. 3. FIG. 5(b) shows protrusions 66 spaced in the same manner around the circumference of surface 63. In this case, the protrusions 66 are oriented at an angle, as shown for guiding a blood sample along the surface 63.

Figure 5C:
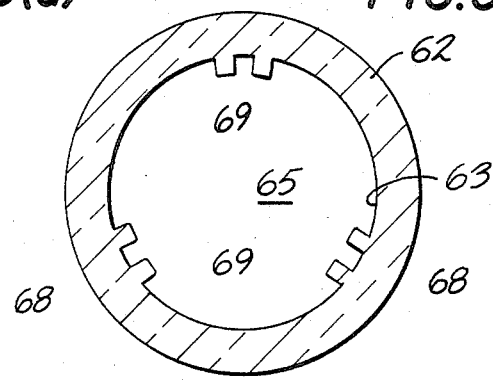
Figures 5D, 5E:
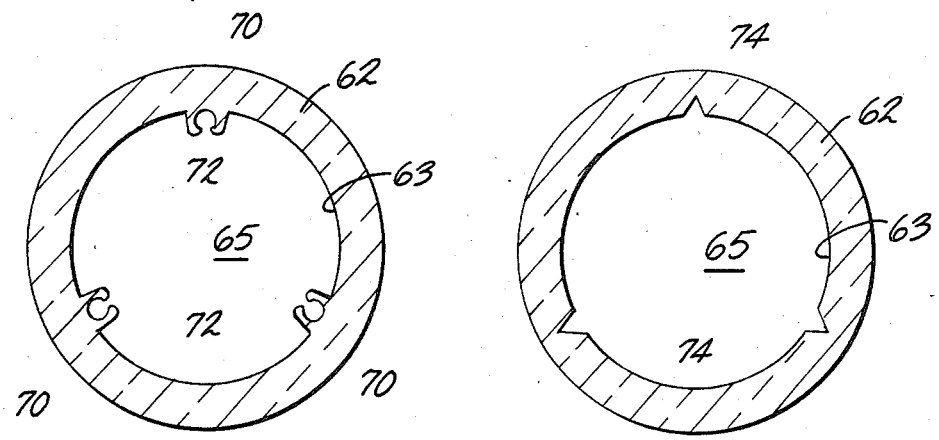

FIG. 5(c) is representative of multiple protrusions 68 which may serve to form a guiding passage 69 therebetween. The embodiments shown in FIG. 5(d) provides protrusions 70 which cooperate as shown to provide a semi-capillary passage 72 therebetween for a more positive direction of the flow of a blood sample along the surface 63. FIG. 5(e), shows an embodiment wherein indentations or depressions 74 are incorporated into the surface 63 for enhancing the passage or flow of blood along the surface 63.

As will be appreciated by practitioners-in-the-art, it is most important for the small quantities of collected blood to be transferred rapidly into the collection container. Otherwise, the blood will clot. With a collector using one of the forms of guiding surface of the invention, the flow of collected blood from tip 28 to area 34 is much more rapid, and an immediate transfer of the specimen from tip 28 to area 34 is achieved.

That is, the average blood microcollection container utilized with the invention herein is 43.18 mm. long. Its internal diameter is 6.17 mm. plus or minus 0.05 mm. Its outer diameter averages 9.71 mm. plus or minus 0.05 mm. The unplugged capacity of the container prior to having a cap placed on the open end thereof is 1.05 ml. plus or minus 0.05 ml. The plugged capacity of the collectors is 0.925 ml. plus or minus 0.025 ml. Since these collection containers are made of a thermoplastic material in order to provide a material which is moldable, the internal surfaces of blood collection containers have a tendency to be hydrophobic. Thus, the various forms and/or embodiments of the invention here serve to enhance the flow of blood along these surfaces. It is conventional, in the past, in order to provide wettability to such surfaces, to include or incorporate additives into the thermoplastic material when it is formed or coat the surface after molding, in order to provide wettability. Of course, these additives contribute to the added cost of such containers, limit their shelf-life, and adversely impact the function of the device by the same cases interacting with the specimen being collected. All of these disadvantages are removed with the use of the device herein, thus making the arrangements herein very attractive from a commercial mass production standpoint. It will be understood, further, that the device of the invention is much more attractive for those who must purchase and use such devices on a continuous basis. Such devices are used throughout the United States, literally in the millions in the course of a year.

Preferably, the various embodiments of the invention will be comprised of a clear molded thermoplastic such as a polypropylene, for example. Other materials which may be used, as will be appreciated by practitioners-in-the-art, include such thermoplastics as polyethylene, polystyrene and polytetrafluoroethylene.

Whereas, as discussed above, specific embodiments of microcollection containers and associated tops or caps have been shown, it should be understood that it is within the purview of this invention to provide other forms of microcollection containers with differently configured cooperating caps or tops, as long as they can be configured to receive the appropriate embodiments of the various elongated flow inducing members of the invention, whether such members are incorporated during the formation in the mold of such microcollection containers with associated tops or whether they are separately formed and placed in or adhered to the microcollection assemblies which are to be used with the inventions herein.

While the forms of apparatus herein described constitute preferred embodiments of the invention, it is to be understood that the invention is not limited to these precise forms of apparatus, and that changes may be made therein without departing from the scope of the invention which is defined in the appended claims. For example, a plurality of longitudinal protrusions or indentations may be spaced equally around the entire collector circumference of a blood collector to give a sectional view of the collector a fluted appearance. Moreover, one or more half length elongated protrusions or indentations may be positioned to extend from the open mouth of the collector to a point half way along the length. Then, one or more half-length elongated protrusions or indentations may extend from the halfway point along the collector to the closed end. However, this second set is off-set from the first set so that liquid following the guiding surface of such protrusions or indentations is forced to "break-up" its pattern half-way along the length of the collector. Thus, mixing of a blood sample with additives in the collector, for example, is enhanced. Other variations for mixing include placing such protrusions or indentations at angles to the axis of the elongated collector reservoir, or arranging the protrusions or indentations in helical paths along the internal surface of the collector.

What is claimed is:

1. A collector for use on a blood microcollection container which collector avoids capillary blood flow, comprising
   (a) a collector body having a blood flow passage therethrough;
   (b) the bottom surface of said blood flow passage being the blood flow surface of said blood flow passage;
   (c) a blood source engaging front end surface on said body;
   (d) a blood discharge rear end surface on said body;
   (e) said body extending from said blood source engaging front end surface to said blood discharge rear end surface;
   (f) means on said body for attaching said body to a microcollection container;
   (g) vent means in said body for air displacement therethrough;
   the improvement characterized by
   (h) an elongated solid blood flow inducing member positioned along said blood flow surface of said blood flow passage;

(f) the forward end of said member positioned midway between said front end surface and said blood discharge rear end surface of said blood flow passage; and (j) the rear end of said member extending beyond said blood discharge rear end surface.

2. The collector of claim 1, further characterized by
(a) said member is solid in cross section.

3. The collector of claim 1, further characterized by
(a) said member is round in cross section.

4. The collector of claim 1, further characterized by
(a) said member is square in cross section.

5. The collector of claim 1, further characterized by
(a) said member is tubular in cross section.

6. The collector of claim 1, further characterized by
(a) said member is a separately formed part adhered along the length thereof to the said blood flow surface of said collector body.

7. The collector of claim 1, further characterized by
(a) said collector is comprised of a molded thermoplastic material; and
(b) said member is an integral part of said molded collector.

* * * * *